United States Patent [19]

Greenfield et al.

[11] Patent Number: 4,950,740
[45] Date of Patent: Aug. 21, 1990

[54] RECOMBINANT DIPHTHERIA VACCINES

[75] Inventors: Lawrence Greenfield, Albany; Anne W. Emerick, Oakland; Walter J. Laird, Pinole, all of Calif.

[73] Assignee: Cetus Corporation, Emeryville, Calif.

[21] Appl. No.: 164,522

[22] Filed: Mar. 7, 1988

Related U.S. Application Data

[63] Continuation of Ser. No. 27,064, Mar. 17, 1987, which is a continuation of Ser. No. 697,860, Feb. 4, 1985, abandoned.

[51] Int. Cl.$^5$ .......................... C07K 13/00; C07K 7/00
[52] U.S. Cl. .................................... 530/350; 530/403;
530/825; 530/300; 514/2; 424/88; 435/172.1;
435/172.3; 935/10; 935/12
[58] Field of Search ................. 530/27, 300, 350, 826,
530/825, 403; 314/2; 435/68, 70, 91, 172.3,
317.1, 320; 424/89, 85, 88; 536/27; 935/10, 12

[56] References Cited

U.S. PATENT DOCUMENTS 4,709,017 11/1987 Collier et al. .

OTHER PUBLICATIONS

Carroll et al., PNAS 81: 3307–3311.
Anderson et al., Infect. & Immunity, 39: 233–238.
Giannini (1984), NAC 12: 4063–4069.
Kaczorek (1983), Science 226: 855–858.
Uchida et al. (1983), J.B.C. 248: 3851–3857.
Greenfield et al. (1987), PNAS 80: 6853–6857.

*Primary Examiner*—Thomas G. Wiseman
*Assistant Examiner*—Anne Brown
*Attorney, Agent, or Firm*—Gregory J. Giotta; Kate H. Murashige; Albert P. Halluin

[57] ABSTRACT

Recombinant diphtheria toxin A fragment muteins which are enzymatically inactive but immunologically crossreactive with diphtheria toxin are disclosed. Intermediates and methods for preparing such proteins using recombinant techniques are also described.

3 Claims, 4 Drawing Sheets

FIG. 1-1

```
                                                          Msp I
                                                       CCGGCCGTTGCG  TATCCAGTGGCTACGACTCAGGTTGTAATGA

Mbo I
TTGGGATGATGTACCTGATCTGAGAGCGAT  TAAAAACTCATTGAGGAGTAGGTCCCGATT  GGTTTTTGCTAGTGAAGCTTAGCTAGCTTT

CCCCATGTAACCAATCTATCAAAAAGGGC   ATTGATTTCAGAGCACCCTTATAATTAGGA

TAGCTTTACCTAATTATTTTATGAGTCCTG  GTAAGGGGATACGTTGCAGCAGAAAACTG   TTTGGCTCAATCTTAATAGGGCGCTACTG
          TerValLeu             ValArgGlyTyrValValSerArgLysLue  PheAlaSerIleLeuIleGlyAlaLeuLeu
                -31                            -21                          -11

GGGATAGGGCGCCCACCTTCAGCCCATGCA  GGCGCTGATGATGTTGTTGATTCTTCTAAA  TCTTTTGTGATGGAAAACTTTTCTTCGTAC
GlyIleGlyAlaProProSerAlaHisAla  GlyAlaAspAspValValAspSerSerLys  SerPheValMetGluAsnPheSerSerTyr
           -1                              10                              20

CACGGGACTAAACCTGGTTATGTAGATTCC  ATTCAAAAAGGTATACAAAAGCCAAAATCT  GGTACACAAGGAAATTATGACGATGATTGG
HisGlyThrLysProGlyTyrValAspSer  IleGlnLysGlyIleGlnLysProLysSer  GlyThrGlnGlyAsnTyrAspAspTrp
           30                              40                              50

AAAGGGTTTTATAGTACCGACAATAAATAC  GACGCTGCGGATACTCTGTAGATAATGAA   AACCCGCTCTCTGGAAAGCTGGAGGCGTG
LysGlyPheTyrSerThrAspAsnLysTyr  AspAlaAlaGlyTyrSerValAspAsnGlu  AsnProLeuSerGlyLysAlaGlyGlyVal
           60                              70                              80

GTCAAAGTGACGTATCCAGGACTGACGAAG  GTTCTCCGACTAAAAGTGGATAATGCCGAA  ACTATTAAGAAAGAGTTAGTTTAAGTCTC
ValLysValThrTyrProGlyLeuThrLys  ValLeuAlaLeuLysValAspAsnAlaGlu  ThrIleLysLysGluLeuGlyLeuSerLeu
           90                              100                             110

ACTGAACCGTTGATGGAGCAAGTCGAACG   GAAGAGTTTATCAAAAGGTTCGGTGATGGT  GCTTCGCGTGTAGTGTCAGCCTTCCCTTC
ThrGluProLeuMetGluGlnValGlyThr  GluGluPheIleLysArgPheGlyAspGly  AlaSerArgValValLeuSerLeuProPhe
           120                             130                             140

GCTGAGGGAGTTCTAGCGTTGAATATATT   AATAACTGGGAACAGGGCGAAAGCGTTAAGC GTAGAACTTGAGATTAATTTTGAAACCCGT
AlaGluGlySerSerValGluTyrIle     AsnAsnTrpGluGlnAlaLysAlaLeuSer   ValGluLeuGluIleIleAsnPheGluThrArg
           150                             160                             170

GGAAAAACCTGGCTCAAGATGCCGATGTGAG TATATGGCTCAAGCCTGTGCAGGAAAATCGT GTCAGGGCGATCAGTAGGTAGTCATTGTCA
GlyLysGlyArgGlyValGlnAlaMetTyrGlu TyrMetAlaGlnAlaCysAlaGlyAsnArg ValArgArgSerValGlySerSerLeuSer
           180                             190                             200

TGCATAAATCTTGATTGGATGCTCATAAGG   GATAAAACTAAGACAAAGATAGAGTCTTTG AAAGAGCATGCCCTATCAAAAATAAAATG
CysIleAsnLeuAspTrpAspValIleArg   AspLysThrLysThrLysIleGluSerLeu LysGluHisGlyProIleGlyAsnLysMet
           210                             220                             230
```

RECOMBINANT DIPHTHERIA VACCINES

This application is a continuation of application Ser. No. 027,064, filed Mar. 17, 1987, which is a file wrapper continuation of Ser. No. 697,860, filed Feb. 4, 1985, now abandoned.

TECHNICAL FIELD

The invention relates to the field of recombinant protein production for use in vaccines. More particularly, the invention relates to enzymatically inactive diphtheria toxin fragments useful in preparing vaccines.

BACKGROUND ART

Children in developed countries are customarily protected against diphtheria using "DPT" vaccine a mixture of immunogens which induce the production of antibodies against diphtheria, whooping cough, and tetanus. Recently problems have arisen with respect to maintaining adequate supplies of this vaccine, apparently due to unwillingness of certain manufacturers to continue manufacturing. The reason for this reluctance is due to liability exposure in connection with lawsuits brought by parents of children having adverse reactions to the vaccine. At least some of these adverse reactions are assumed to be due to impurities in the vaccines.

The diphtheria component of the DPT vaccine ls a toxoid produced by treating diphtheria toxin obtained from *Corynebacterium diphtheriae*, its natural source, with denaturants that permit its immunogenicity to be retained, while inactivating its cytotoxic properties. As this preparation involves the isolation of protein from natural sources and treatment of the mixture with non-specific reagents, such as glutaraldehyde, a heterogeneous material ordinarily results. This presents a quality assurance problem which, evidently, has not yet entirely been solved.

Recombinant techniques offer a useful alternative to isolation of the native material. These techniques can be used to produce desired proteins which are free of those impurities that would ordinarily accompany the materials obtained from natural sources. In addition, recombinant techniques permit manipulation of the sequence of amino acids so as to confer desired properties on the product. Both of these advantages of recombinant protein production have been found relevant to the production of a superior diphtheria vaccine.

The entire coding sequence of diphtheria toxin (DT) has been cloned, and portions of it have been expressed in *E. coli* in practical amounts (Greenfield, L., et al, *Proc Natl Acad Sci* (1983) 80:6853–6857; Ratti, G., et al, *Nucleic Acids Res* (1983) 11:6589; Leong, D., et al, *Science* (1983) 220:515; Tweten, R. K., et al *J Bacteriol* (1983) 156:680).

The general characteristics of the toxin are well understood. DT is a typical toxin having an "A" fragment which is cytotoxic and "B" fragment responsible for its binding, and, possibly, translocation properties. DT is secreted from *Corynebacterium diphtheriae* as a single polypeptide chain containing 535 residues. The approximately 193 residue sequence at the amino terminus is considered the A fragment; it is cytotoxic, because cf its enzymatic activity in catalyzing the transfer of ADP-ribose from NAD to elongation factor-2 (EF-2) thereby blocking protein synthesis and causing cell death. The carboxy-terminal, approximately 342 residue, sequence is considered the B portion and is not only associated with binding the cytotoxic portion to the cell but also presumably contains functions which permit translocation of the A fragment into the intracellular environment. The entire amino acid sequence of the naturally occurring toxin has been deduced from the coding sequence, and is set forth in FIG. 1. It is believed that cleavage after one of the Arg residues at positions 190, 192 or 193 (trypsin is capable of thus cleaving in vitro) is required for intoxication of cells. This alteration is believed to be followed by breakage of the disulfide bond between cysteine at position 186 and the cysteine at position 201 to liberate the A and B fragments from each other. Once released inside the cell, a single molecule of fragment A can be lethal for the individual cell (Yamaizumi, M., et al, *Cell* (1978) 15:245).

It is believed that the hydrophobic sequence of approximately 32 amino acids in the vicinity of residue 350 is responsible for the translocation properties of B chain. A cross-reacting mutant secretes "CRM 45", a modified form of DT which contains approximately half of the B portion at the N-terminal end. CRM45 is capable of insertion into artificial lipid bilayers under appropriate in vitro conditions to form ion conductive channels (Kagan, B. L., et al, *Proc Natl Acad Sci (USA)* (1981) 4950; Donovan, J. J., et al, ibid (1981) 78:172 Kayser, B., et al *Biochem Biophys Res Commun* (1981) 99:358). In addition, the 25 (32) amino acid region referred to above was earlier identified by Lambott, P., et al, *J Cell Biol* (1980) 8:837 as especially hydrophobic, and to resemble transverse lipid-associating domains found in intrinsic membrane proteins.

Other cross-reacting mutants have been disclosed. One of them, CRM197, is capable of binding target cells, but does not kill them. CRM197 has been shown to be enzymatically inactive, and to be nontoxic to guinea pigs (Uchida, T., et al, *J Biol Chem* (1973) 248:3838–3844). The gene encoding CRM197 has been sequenced, and shown to possess a single mutation in its A portion (Giannini, G., et al, *Nucleic Acids Res* (1984) 2:4063–4069).

It has also been shown recently that the glutamic acid residue at position 148 is critical to the active site (Caroll S. F., et al, *Proc Natl Acad Sci (USA)* (1984) 81:3307–3311). When NAD+ is chemically linked to glu-148 of native diphtheria toxin A fragment, enzymatic activity is lost. Inactivation of the A portion of DT offers the opportunity to provide a non-toxic protein which retains the immunogenicity of the native material.

The disadvantages of the currently available, relatively impure toxoid-based diphtheria component of the DPT vaccine could be overcome by the use of recombinant protein. The current toxoid preparations require stringent monitoring for toxicity, and, because glutaraldehyde linkage is random, are heterogeneous products. The recombinant vaccine provides increased yields of pure product without the necessity of time-course toxicity tests, due to the opportunity to modify specifically the toxic component to destroy its enzyme activity. The inactive A fragment is thus available as a homogenous preparation.

DISCLOSURE OF THE INVENTION

The invention provides a means to obtain in a practical, economic manner, a homogeneous, safe, and effective immunogenic protein capable of causing the formation of neutralizing antibodies against diphtheria toxin in vaccinated subjects. The vaccine contains an A diphtheria toxin fragment which has been modified to destroy its cytotoxicity, but regains its ability to raise the appropriate immunoglobulins. This A fragment can be used as a vaccine either alone, or bound to a native or modified B chain to mimic the entire toxin molecule. In either case, nontoxicity is assured by crippling the A fragment activity.

Accordingly, in one aspect, the invention relates to a protein comprising a diphtheria A (DT-A) fragment mutein that lacks enzymatic activity, and which is cross-reactive immunologically with native A chain. Such proteins are useful as anti-diphtheria vaccines. In additional aspects, the invention relates to DNA sequences, recombinant vectors, organisms and methods useful in producing the desired DT-A muteins. In still another aspect, the invention relates to a method of protecting a subject mammal against a diphtheria infection by administering effective amounts of a vaccine prepared from the inactivated DT-A mutein.

BRIEF DESCRIPTION OF THE DRAWINGS

FIG. 1 shows the DNA and amino acid sequence for diphtheria toxin produced by *C. diphtheriae*.

MODES OF CARRYING OUT THE INVENTION

A. Definitions

As used herein, "diphtheria toxin A fragment (DT-A)" refers to an amino acid sequence similar to that set forth in FIG. 1 comprising the N-terminal approximately 193 amino acids. The sequence may be somewhat longer or shorter; e.g., in the examples below, five additional amino acids of the B chain are included. The DT-A muteins of the invention are referenced against the DT-A as shown in FIG. 1 by indicating the number of the position altered, and the alteration obtained. For example, des-glu$_{148}$ DT-A has the same sequence as that shown in FIG. 1 except that the glutamic acid at position 148 has been deleted. Similarly Asn$_{148}$ DT-A refers to a protein of this sequence, except that the glutamic residue at position 148 has been replaced with asparaqine; Gly$_{158}$ DT-A has qlycine rather than alanine at position 158.

"Whole" toxin protein refers to combinations of A and B fragments which are associated as originally produced or are reconstituted from separate A and B portions. In some cases, the A and B portions may be linked covalently, such as through a disulfide bond, however covalent linkage is apparently not necessary for effective association. (The —SH groups may be blocked by, for example, acetylation, and the fragments are still capable of reconstitution into "whole" toxin.)

A "non-conservative amino acid alteration" refers to the deletion or replacement of an amino acid residue wherein the deletion or replacement causes loss of biological activity.

Two proteins are "cross-reactive" with each other in immunological reactions if they both contain epitopes reactive with the same antibody. Such cross-reactivity may be ascertained using standard competition immunoassays between the proteins for the same antibody preparation. However, proteins which are cross-reactive antigenically against a particular antibody as shown by the competition assays are not necessarily "immunogenically" cross-reactive. To be immunogenically cross-reactive, antibodies raised against one must react with the other. The nature of the antibodies raised depends on which domains are immunodominant and which are immunorecessive. In the context of the invention, the DT-A muteins or proteins of which they are a part must be cross-reactive with native diphtheria toxin in the sense that antibodies raised against the muteins or their protein conjugates must react with native diphtheria toxin, just as the antibodies raised against the current toxoid vaccines are capable of doing so. However, the ability of the mutein to cross-react antigenically against antibodies raised against diptheria toxin A fragment in rabbits or against diphtheria toxoid raised in horses is germane to this final criterion. Such reactivity can be shown by immunoassay methods known in the art, such as ELISA, RIA, and Western blot.

"Enzymatically active" DT-A refers to DT-A which is active in catalyzing the transfer of ADP-ribose from NAD to EF-2, and thus is capable of a positive response in to the standard assay for DT-A according to the method of Chung, D. W., et al, *Infect Immun* (1977) 16:832–841. "Enzymatically inactive" fragments are not responsive in this particular assay.

B. General Description

The DT-A muteins of the invention are encoded by DNA sequences produced by alteration of cloned DNA which encodes the native amino acid sequences shown in FIG. 1. Such alterations are most conveniently produced by site specific mutagenesis, a technique which is now standard in the art. The technique is performed by ligating a double stranded segment of the DNA to be altered into a double stranded form (RF) of the M-13 cloning vector. Single stranded M13 phase DNA is then harvested and used as a template after annealing to a complementary DNA sequence. The synthesis employs a 11–30 nucleotide primer which is defectively complementary to the desired sequence--i.e., is complementary to large sections of the sequence to be altered, but contains a mismatch corresponding precisely to the desired set of nucleotide residues. The short double stranded segment is lengthened using DNA polymerase (Klenow). The resulting double stranded DNA, which will be complementary except for the desired altered region is then transformed into phase-supporting host bacteria. Cultures of the bacteria are plated so as to permit plaque formation from single cells which harbor the phase. Theoretically 50% of the plaques will contain phase with the mutated form; 50% will have the original sequence. In the usual assay the plaques are distinguished by hybridization with kinased synthetic primer under stringency conditions permitting binding only for perfectly matching strands. The successfully hybridizing plaques are then picked, cultured, and the DNA recovered.

Prehybridization and hybridization procedures are known in the art. In a typical procedure, plaque DNA is fixed to the filter by sequential treatment for 5 min with 500 mM NaOH, 1.5 M NaCl, and are washed twice for 5 min each time with 5 × standard saline citrate (SSC). Filters are air dried and baked at 80° C. for 2 hr. The duplicate filters are prehybridized at 42° C. for 6–8 hr with 10 ml per filter of DNA hybridization buffer (5×SSC, pH 7.0 5× Denhardt's solution (polyvinylpyrrolidine, plus Ficoll and bovine serum albumin; 1x =0.02% of each), 50 mM sodium phosphate buffer at pH 7.0, 0.2% SDS, 20 μm/ml Poly U, and 50 μg/ml denatured salmon sperm DNA).

The samples are hybridized with kinased probe under conditions which depend on the stringency desired. Typical moderately stringent conditions employ a temperature of 42° C. for 24-36 hr with 1-5 ml/filter of DNA hybridization buffer containing probe. For higher stringencies high temperatures and shorter times are employed. The filters are washed four times for 30 min each time at 37° C. with 2×SSC, 0.2% SDS and 50 mM sodium phosphate buffer at pH 7 then are washed twice with 2×SSC and 0.2% SDS, air dried, and are autoradiographed at −70° C. for 2 to 3 days.

The coding sequence corresponding to the native DNA is shown in FIG. 1. Suitable oligomers containing the desired sequences are conveniently synthesized using standard techniques for oligomer synthesis, including commercially available automated instruments. Such methods are capable of synthesizing oligomers containing up to approximately 40 nucleotides. Sequences cf any desired length may be prepared from overlapping complementary shorter single stranded portions cf alternate sense and anti-sense strands using DNA polymerase. See, e.g., Edge, M. D., et al, *Nature* (1981) 292:756; Nambiar, K. P., et al, *Science* (1984) 223:1299; Jay, E., et al, *J Biol Chem* (1984) 259:6311.

Amino acid residue deletions, insertions, or replacements which affect the active site are particularly preferred, as these are most directly assured to inactivate the protein. The active site is known to include the glutamic acid residue at 148. Amino acid substitutions, deletions or insertions at this location result in an inactive protein which, however, retains cross-reactivity with the native molecule. Similar alterations within approximately 15 amino acids either side of this residue are also expected to result in such inactive proteins.

When the desired altered coding sequence is obtained it is ligated into expression vectors suitable for production of the recombinant protein in transformed hosts. Useful expression vectors for DT-A specifically are illustrated below. These expression vectors are particularly suited for procaryotic hosts; however, means to prepare expression vectors for known coding sequences operable in eucaryotes are known in the art, and techniques for effecting expression in hosts transformed with these vectors are also known. Therefore, the peptides and expression vectors of the invention are intended to include those produced by, or operable in a variety of hosts, not just bacteria. The recombinant proteins are produced under standard culture conditions, and isolated from the culture using standard protein purification techniques appropriate to the form of production. When produced intracellularly as mature proteins, the protein is recovered by lysing or sonicating or in any other manner disrupting the cells, and subjecting the disruptate to standard purification procedures. The protein thus produced, depending on the nature of the expression system may or may not be soluble and the specific procedures applied will depend on this characteristic. If the encoded protein is properly linked to leader sequences operable in a eucaryotic or gram-positive host, production may also be obtained wherein the desired protein is secreted into the medium, and under these circumstances it may be recovered by separating the cells from the supernatant culture fluid. In any event, for use in a vaccine, the recombinant DT-A mutein must be supplied in purified form.

"Purified" refers to the absence of materials ordinarily associated with the "purified" material in its native state. Thus, "purified" DT-A mutein refers to preparations free of proteins ordinarily associated with this protein as produced by Corynebacter. Trace amounts of materials associated with the recombinant host, but not present in the native protein producing strain may be present. However, the B chain of diphtheria is specifically excluded from this definition as it may enhance the value of the resulting vaccines.

The product DT-A muteins may be directly formulated into vaccine preparations using standard formulation methods or may first be recombined with H chain in order to mimic more accurately the nature of the diphtheria toxin itself. The recombination with B chain may be done either on a protein or on a DNA level.

If carried out on a protein level, the DT-A mutein is treated in the presence of a reducing agent such as β-mercaptoethanol or dithiothreitol (DTT) with a material containing B chain. B chain may be obtained from native toxin-like materials such as CRM 197, pretreated with trypsin. The mixtures are then dialyzed and sized to separate associated and nonassociated fractions.

For use as a vaccine, the DT-A muteins of the invention are administered to mammalian subjects susceptible to diphtheria infection in amounts comparable to those for the toxoid ranging from 0.05–5 μg per kg body weight, usually administered in three doses. The size of the dose will depend on the nature of the subject, and on the subject's immunological status.

C. Example the following example is intended to illustrate but not to limit the invention.

C.1. Isolation of Coding Sequences for DT-A

DNA was isolated from corynephate $\beta^{Tox+}$ grown on *Corynebacterium diphtheriae* C7$^{(-)tox-}$. (The host and phase are obtainable from J Collier, Harvard University: Tweten, R. K., et al, *J Bacteriol* (1983) 156:680.)

To prepare DNA, high-titered β phage stocks were prepared in "TYE' medium" (15 g/l bactotryptone, 10 g/l yeast extract 5 g/l NaCl supplemented with 1 mM CaCl$_2$) by the method of Holmes, R. K., et al, *J Virology* (1969) 38:586. Upon completion of lysis, debris was removed by centrifugation at 13,000×g for 5 min, and NaCl added to 0.5 M, followed by PEG to 100 g/l, and the mixture was stirred overnight at 4° C. The phage were concentrated by centrifugation at 13,000×g for 15 min and resuspended in 100 mM Tris HCl PH 7.5, 100 mM NaCl, 20 mM EDTA. Pronase was added to 1 mg/ml and the mixture was incubated at 37° C. for 2 hr. After removal of PEG by addition of Potassium phosphate (⅔ dibasic, ⅓ monobasic) to 23% and centrifugation at 6,000×g for 5 min, the lower phase was extracted with phenol/ethanol precipitated and the DNA purified by banding in a CsCl-EtBr gradient.

Approximately 500 μg of the phage DNA (MW=22×10$^6$ daltons) was treated with EcoRI and XbaI and the resulting mixture run on 1.7 liters 1% agarose gel at 90 volts for 35 hr. The XbaI/EcoRI fragment (1.5 ×10$^6$ daltons) containing the toxin gene was cut out, run through a syringe, and electroeluted in 1/10 TBE for 4 hr at 500 volts onto a spectropore dialysis membrane. The DNA was retrieved from the membrane using 0.25% SDS in 1/10 TBE, phenol extracted, ether extracted, and ethanol precipitated.

To prepare and clone the "Mbo fragment", the resulting DNA was further restricted with MboI, the DNA resolved on 5% PAGE, and the 831 bp fragment isolated and cloned into pBR322 which had been BamHI restricted and BAPped. The desired recombinant plasmid was designated pMbo. However, directly isolated Mbo fragment was used for the constructions below.

Figure 2:
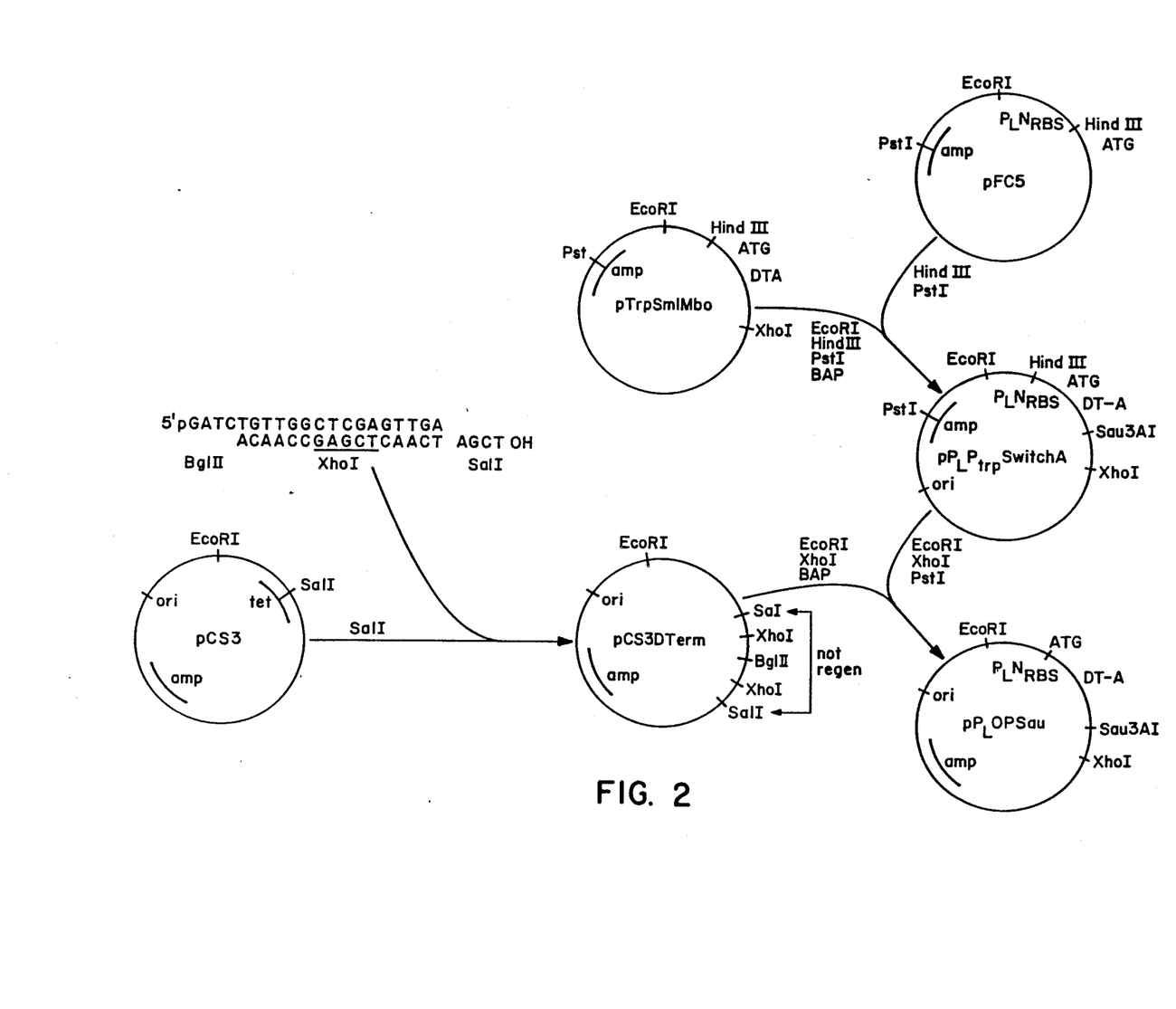
FIG. 2 shows the construction of pPLOPSau.
Figure 3:
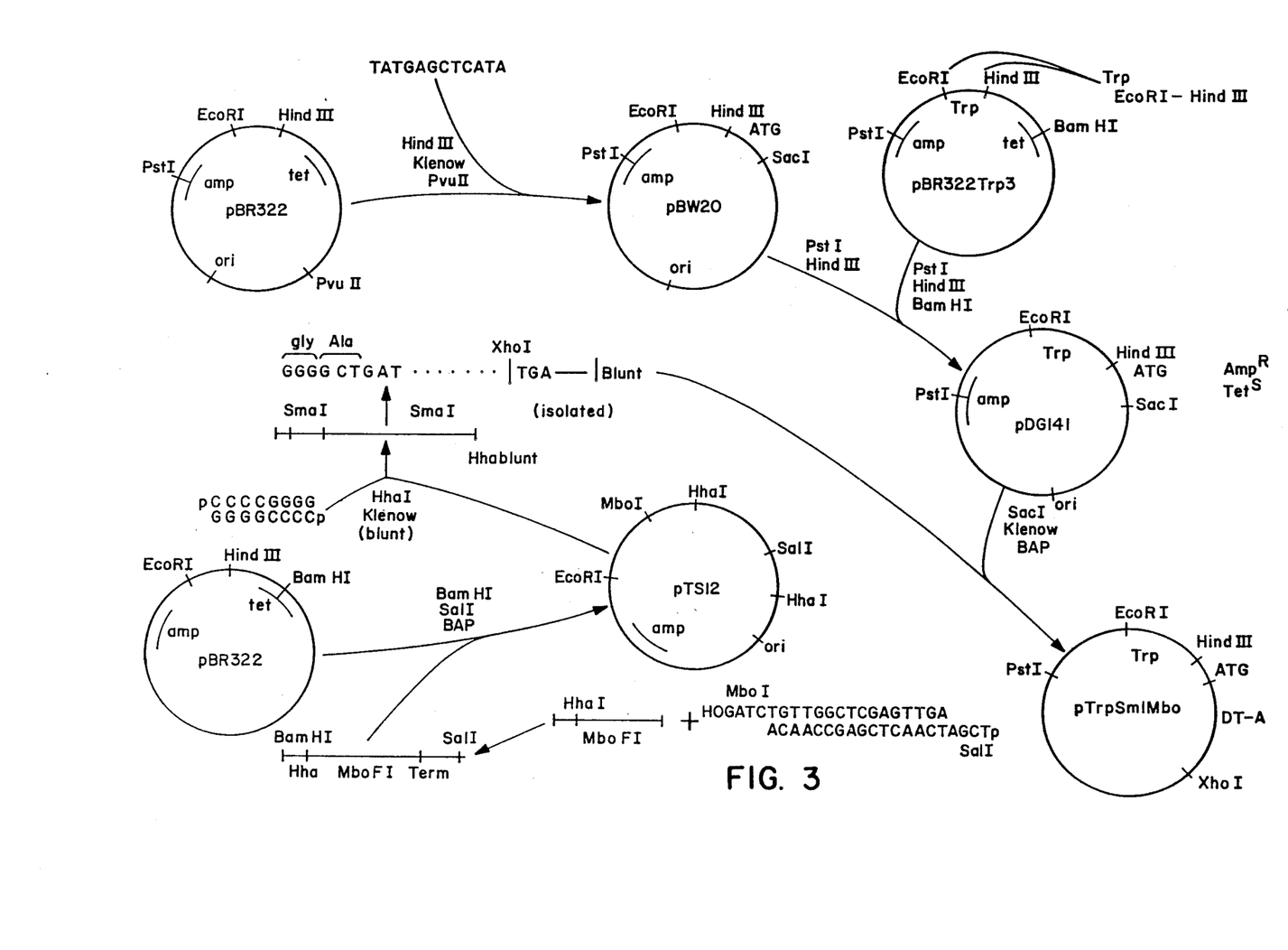
FIG. 3 shows the construction of pTRPSmlMbo.

C.2. preparation of Expression Vectors for DT-A pP<sub>L</sub>OPSau which contains the coding sequence for DT-A was constructed as outlined in FIG. 2.

To provide a properly terminated DT-A fragment, the synthetic oligonucleotide

GA TCT GTT GGC TCG AGT TGA

Arg Ser Val Gly Ser Ser Term which encodes the six amino acids normally found sequential to the Arq at position 193 of native DT and a stop codon, was kinased and annealed to a complementary sequence to give the double stranded sequence:

```
5'P GATCTGTTGGCTCGAGTTGA
       ACAACCGAGCTCAACTAGCT OH5'
    BglII      XhoI        SalI
``` as shown in FIG. 2. The fragment has a phosphorylated BglII site and a non-phosphorylated SalI site. This fragment was ligated with SalI digested pCS3 (ATCC 39142) a high copy number plasmid at elevated temperatures to obtain pCS3DTerm, which results from ligation of an inverted duplication of the synthetic oligonucleotides (formed by annealing the BGlII ends of two of the synthetic oligonucleotides) to insert a symmetrically duplicated termination sequence pair. The vector fragment from EcoRI/XhoI digestion of pCS3DTerm (see FIG. 2) thus provides that portion of the termination sequence downstream from the XhoI site. The thus digested BAPed vector from pDC3DTerm was ligated with a fragment containing the P$_L$N$_{RBS}$ cassette operably linked to the DT-A fragment and the upstream of XhoI portion of the termination sequence. This latter fragment is obtained by EcoRI/XhoI (PstI to prevent religation) digestion of pP$_L$P$_{trp}$ SwitchA (see below). The resulting plasmid, pP$_L$OPSau, includes the P$_L$N$_{RBS}$ sequence immediately preceding the ATG start codon for DT-A linked to mature protein encoding sequence of Mbo with its terminator.

Intermediate Plasmids:

pP$_L$P$_{trp}$SwitchA is prepared from pTrpSmlMbo (see below) and-pFC5 as follows (see FIG. 2):

Fifty-five μg pTrpSmlMbo was restricted with EcoRI, HindIII and PstI, and the vector portion treated with BAP. Five μg of the vector fragment was ligated to 5 μg of HindIII/pstI digested pFC5. Three tenths μg of the ligation mixture DNA was transformed into a lambda lysogen strain of E. coli MC1000, (ATCC 39531) cells. Amp$^R$ clones selected and the desired construction confirmed by restriction analysis, and designated pP$_L$P$_{trp}$ SwitchA. (Growth of these transformants on TYE' medium containing 100 μg/ml ampicillin at 30° C. for 7 hr, followed by heating to 60° C. to raise quickly the medium temperature to 42° and growth at 42 for 1 hr resulted in production of DT-A at a concentration of 5–20 μg/ml as assayed by the procedure of Chung, et al, Infect Immun (1977) 16:832.)

pTrpSmlMbo contains the DT-A fragment coding sequence followed by the Mbo terminator sequence (supra) under the control of the trp promoter. The construction is from pTS12 (a plasmid containing the DT-A and Mbo terminator) and pDG141 (ATCC 39588), which contains the trp promoter upstream of ATG on a modified pBR322 vector (see FIG. 3).

53.5 μg of pTS12 (see below) was restricted with HhaI, blunt-ended with Klenow, and 18 μg of the resultant fragments ligated to 3.15 nmoles of phosphorylated oligomeric linker CCCCGGGG, and then treated with SmaI. The resulting sequence at the 5' terminus was thus modified to give the sequence GGGGCTGA which encodes the peptide sequence beginning with amino acid 1 of the DT-A fragment (see FIG. 3). The 3' end of the ligation product terminates in the first HhaI site of pBR322 following the SalI site, and the fragment contains the entire DT-A coding sequence in reading frame with terminator for the small Mbo fragment. The desired 654 bp fragment was then isolated following 6% polyacrylamide gel electrophoresis using the crush and soak method.

One picomole of this modified prepared fragment was ligated with 0.7 μg (0.4 pmoles) of pDG141 which had been restricted with SacI, blunt-ended with Klenow, and BAPed. The pDG141-derived fragment has an ATG start codon operably linked to the trp promoter. The resulting ligation mixture was transformed into *E. coli* MM294, and resistant colonies grown in 10 ml TYE' medium containing 100 μg/ml ampicillin and screened for plasmid size. Those colonies which contained plasmids larger than pDG141 were screened for expression of the DT-A fragment. The cells were grown to log phase in 10 ml TYE; medium containing 100 μg/ml ampicillin at 37° for 4 hr. One ml of cells was centrifuged and the pellet resuspended in 20 μl of buffer containing 62.5 mM Tris pH 6.8 3% SDS. Following heating at 95° C. for 5 min, the samples were run on a 12.5% SDS polyacrylamide 3% stacking gel according to Laemmli (*Nature* (1970) 227:680). Two clones which showed an additional protein band at the expected molecular weight were confirmed by measuring the EF-2 ADP-ribosylation activity, according to the procedure of Chung, D. W., et al, *Infect Immun* (1977) 16:832. These colonies, designated pTrpSmlMbo produced 20 μg of DT-A per ml culture. The molecule weight and antigenicity of the product were confirmed by Western Blot.

To construct pTS12 the oligonucleotide

GA TCT GTT GGC TCG AGT TGA

Arg Ser Val Gly Ser Ser Term which encodes the amino acid sequence subsequent to the Mbo cleavage site for six additional amino acids prior to a termination codon was synthesized, kinased and hybridized to the complementary synthetic fragment as described above in connection with pCS3DTerm synthesis. One pmole double-stranded oligonucleotide was placed in a three-way ligation mixture with 1.4 pmoles (0.8 μg) of Mbo fragment and the vector fragment formed from 1 μg pBR322 which had been treated with BamHI, SalI, and BAP. The mixture was ligated overnight before transforming into *E. coli* MM294. $Amp^RTet^S$ colonies were selected and the desired construction confirmed by DNA isolation restriction analysis and DNA sequencing. The desired plasmid was designated pTS12.

C.3. Construction of Additional Expression Vectors for DT-A Fragment and for Its Muteins pPLOPSau contains the entire coding sequence of the DT-A fragment (terminated after amino acid 199 and having an XhoI site proximally upstream of the termination codon) in operable linkage to the $P_L$ promoter and N gene ribosome binding site. The control sequences are preceded by an EcoRI site, and the ATG start codon is preceded by a HindIII restriction cleavage site as shown in FIG. 2. pPLOPSau is used both as an expression vector for DT-A in unaltered form, and as a starting material for the preparation of coding sequences and expression vectors for the muteins of the invention.

To facilitate screening for successful mutants, the coding sequence for DT-A is placed under control of the trp promoter. pPLOPSau is therefore converted to pTRPSau by replacing the $P_L$ promoter/$N_{RBS}$ with the corresponding trp promoter region. The trp promoter region is available as an EcoRI/HindIII cassette from pTRP3, a pBR322 derived plasmid deposited with ATCC on 18 December 1984 and having accession number 39946. pTRP3 is treated with EcoRI/HindIII, and the small fragment isolated. This fragment is ligated with the vector fragment from EcoRI/HindIII digested pPLOPSau and the ligation mixture transformed into *E. coli* MM294 to $Amp^R$. The plasmid DNA from successful transformants was isolated and correct construction confirmed by restriction analysis.

To provide the substrate for mutation, pTRPSau was digested with EcoRI and XhoI in order to excise the control sequences and most of the coding sequences, including that portion of the coding sequence containing the location for the desired mutation. The EcoRI/XhoI small fragment was isolated and ligated into EcoRI/XhoI digested M13-mp8 which had been modified to contain a XhoI site at approximately the location of its native SalI site. (This modification was done by annealing the synthetic double stranded A-fragment-terminating sequence used to construct pCS3DTerm into the SalI site, screening for inserts, and confirming construction by XhoI digestion.) The resulting M13-DT-A was used to serve as a template for oligonucleotide directed mutagenesis to convert the coding sequence for DT-A into those for the muteins.

Des-Glu$_{148}$ DT-A Mutein

To prepare the coding sequence for des-glu$_{148}$ DT-A (designated AE18 herein) 40 pmoles of the oligonucleotide 5 '-GTTATTAATATAAACGCTAG-3' was kinased under standard conditions for use as primer and probe. Ten pmoles of the kinased primer was hybridized to 1 pmole of single stranded (ss) M13-DT-A DNA in 15 μl of a mixture containing 100 mM NaCl, 20 mM Tris-HCl, pH 7.9, 20 mM MgCl$_2$, and 20 mM β-mercaptoethanol by heating at 67° C. for 3–5 min and 37° C. for 30 min. The annealed mixture was chilled on ice and adjusted to a final volume of 25 μl in a reaction mixture containing 0.5 mM of each dNTP, 17 mM Tris-HCl, pH 7.9, 17 mM MgCl$_2$, 83 mM NaCl, 17 mM β-mercaptoethanol, 5 units of DNA polymerase I, Klenow fragment, 0.5 mM ATP, and 2 units of T$_4$ DNA ligase, incubated at 37° C. for 5 hr. The reactions were terminated by heating to 80° C. and the reaction mixtures used to transform competent DG98 cells (ATCC 39768), plated onto agar plates, and incubated overnight to obtain phage plaques.

Prior to conventional probing with primer, the plaques were assayed for the mutated form of the DT-A fragment by ascertaining lack of enzymatic activity in the assay of Chung, et al (supra). The plaques were grown in microtiter plates first in enriched media to obtain adequate supplies of phase, and then on minimal medium lacking tryptophan to activate expression under control of the trp promoter. Microtiter plates containing the cultures on minimal medium were frozen and thawed several times to extract the cell contents, and then treated with the substrate mixture for assay of DT-A activity, including radiolabeled NAD. The microtiter wells were duplicated onto 10% TCA paper to precipitate all proteins, the papers washed with 5% TCA, and then exposed to film. Positive enzymatic activity results in binding of labeled NAD to the protein EF-2, and thus to the paper, giving a positive result. As expected, of approximately 700 plaques assayed, most were positive for enzyme activity (unmutated), and only 9 candidates showing no enzymatic activity were obtained. These plaques were then probed using kinased primer using standard prehybridization and hybridization conditions at high stringency (42° C. for 8 hr). Three of the plaques had positive hybridizations. One plaque which hybridized to primer was picked, cultured and sequenced. This plaque was designated M13-AE18, and contains the coding sequence for des-glu$_{148}$ DT-A.

M13-AE18 was used to construct the expression vector pAE18. M13-AE18 was digested with HindIII and XhoI and the fragment containing the coding sequence isolated. The fragment was ligated with HindIII/XhoI digested pPLOPSau (to provide the control sequences, high copy number vector, and C-terminal codons) and the ligation mixture transformed into lambda lysogen *E. coli* MC1000 (ATCC 39531) to $Amp^R$. DNA from one of the successful transformants was isolated, and correct construction for pAE18 containing the coding sequence for the desired mutein under control of the $P_LN_{RBS}$ control sequences was verified by hybridization to probe (supra). The plasmid pAE18 in was deposited with ATCC on January 1986, and has accession number 53008.

Gly$_{158}$ DT-A Mutein

Two of the six plaques lacking DT-A enzymatic activity but failing to hybridize to probe were further analyzed. One of the plaques, upon DNA sequencing showed that the codon for alanine at position 158 had been mutated to that for glycine, i.e., the coding sequence obtained in this plaque was that for Gly$_{158}$ DT-A.

Digestion of DNA from this plaque with HindIII and XhoI, and ligation cf the fragment into HindIII/XhoI digested pPLOPSau yields pAE2O, the expression vector for Gly$_{158}$ DT-A. Protein obtained from cultured plaques containing this sequence is enzymatically inactive and is cross-reactive with DT-A against antibodies raised against diphtheria toxin.

Asn$_{148}$ DT-A Mutein

To prepare the coding sequence for Asn$_{148}$ DT-A, M13-DT-A (AE16) was again subjected to site-specific mutagenesis in a precisely analogous process, but using the primer 5'-GTTATTAATATAGTTAACG-CTAG-3'. Candidate plaques were ascertained by screening for inactive DT-A production as above. Of 700 plaques, 4 were inactive; all hybridized to kinased probe.

One of these mutagenized M13-DT-A plaques which hybridized with probe was designated M13-AE16, picked, cultured, and used to prepare expression vector pAE16, from pPLOPSau, exactly as described above for pAE18.

C.4. Expression of DT-A Muteins in *E. coli*

Each of pAE16, pAE18, pAE20, and pPLOPSau were transformed into *E. coli* strain MC1000 λ lysogen $N_7N_{53}cI_{857}SusP_{80}$. This host was deposited 21December 1983 and given ATCC number 39531.

The transformed E. coli, selected for were Amp^R were grown in minimal medium at 30° C. with rotary shaking at 250 rpm, and induced at 42° C.

After induction for 4 hr, cells were spun at 10,000×g, and the pellet was resuspended to 1% of the original volume in 50 mM Tris HCl, 30 mM EDTA, 50 mM mercaptoethylamine pH 8.2. The cells were lysed by French press cell disruption at 10,000 psi and sonication. For pAE18 and pPLOPSau, the supernatant pressate was dialyzed against 5 mM sodium phosphate, 30 mM EDTA, 50 mM MEA, pH 6.8 (FA buffer) and passed over a Sephacryl S-200 (Pharmacia) column, and eluted with FA buffer. The eluate was collected in 2 ml fractions and peak fractions located by 13.3% polyacrylamide gel electrophoresis with SDS, pooled, concentrated by Amicon filtration at 35 psi, and samples stored at 4° C.

Upon analysis, the pooled peak fractions in each case represented approximately 26 mg/l expression of DT-A protein which was approximately 50-70% pure.

C.5. Characterization of Recombinantly Produced Muteins

The purified DT-A, des-glu$_{148}$ DT-A (A18) mutein was characterized according to enzymatic activity and cross-reactivity with DT-A, and according to cytotoxicity with and without association with B fragments in comparison to native (nDT-A) and recombinant (cDT-A) A fragment.

Enzymatic Activity

The enzymatic activity was measured according to the method of Chung, et al (supra). While DT-A prepared from pPLOPSau has linear activity from 10–200 ng/100 μl assay volume, similar to native DT-A, A18 had no measurable activity at concentrations up to 25,000 ng/100 μl assay.

Cytotoxicity

Cytotoxicity was measured both for the A proteins alone, and for these proteins in association with B fragments. CRM197 was used as the source of the wild type B fragment.

The whole toxin proteins were formed as follows:

CRM197, which is enzymatically inactive, but contains native B fragment, was separated to A and B fragments by treating approximately 80% pure CRM197 in 10 mM DTT with trypsin to a final concentration of 1 ng/ml for 3 min at 25° C. The reaction was stopped by adding soybean trypsin inhibitor to 10 ng/ml. Final concentration of treated CRM197 was 165 μg/ml.

Samples containing either AE18 or DT-A in 10 mM DTT were mixed with the above reaction mixture containing CRM197 and incubated at room temperature for 15 min before dialyzing against phosphate buffered saline, pH 7.4, to remove reducing agent and permit disulfide bond formation according to the method of Uchida, T., et al, *J Biol Chem* (1973) 248:3851–3854.

To determine the extent of association of A fragment with CRM197 B fragment, each of the A fragments above was first iodinated with iodine-125 and mixed with CRM197 using various ratios of A:CRM197, but maintaining the concentration of iodinated A protein constant at $1.97\times10^{-7}$ M and $10^6$ cpm. Aliquots of these reaction mixtures were electrophoresed with and without reducing agent, to give bands corresponding to unassociated A fragment (24 kD) unassociated B fragment (37 kD) and associated A and B toxin fragments (62 kD). The bands were cut and counted and percent association determined from total cpm in the three hands. Under optimal conditions, maximum DT-A with CRM197 B association was 60%; maximum association of AE18 with B fragment was only 20%.

Based on these association maxima, reconstituted whole toxins were formed containing 74.4 μg of CRM197-associated A18 in 2.9 ml and 0.74 μg of CRM197-associated DT-A in 1.2 ml. Cytotoxicity of these samples was tested both in vitro and in vivo. In the in vitro test, inhibition of protein synthesis as a function of toxin concentration was measured when the test materials were added to cultures of ATCC CCL-81 (VERO) cells according to the method of Gilliland, D. G., et al, *Proc Natl Acad Sci* (1978) 75:5319–5323, and a 50% tissue culture inhibitory dose (TCID 50) was calculated. All non-associated A fragments and CRM197 were nontoxic at concentrations of greater than $1\times10^{-6}$ M. The toxin assembled from DT-A and CRM197 B fragment (assuming 70% A/B association) was toxic between 0.01 and $0.1\times10^{-12}$ M. Whole CRM197-AE18 toxin was non-toxic at concentrations of $20.7\times10^{-9}$ M. Thus, the mutein derived toxin is at least $2\times10^5$ times less cytotoxic against VERO cells.

For the in vivo assay, Dunkin Hartley albino guinea pigs having an average weight cf 666 g were each injected interperitoneally with the samples in the amounts prepared above, using three test animals per sample. The results are shown in Table 1 below:

TABLE 1

| Sample | μg/Kg(1) | (MLD)(2) | Response(3) |
|---|---|---|---|
| Reconstituted: | | | |
| nDT-A:CRM197 | 1.06 | 10.6 | ⅔ death<br>⅓ no killing* |
| cDT-A:CRM197 | 1.06 | 10.6 | 3/3 death |
| AE18:CRM197 | 106.35 | 1063.5 | 3/3 no killing |
| AE18 | 1836.43 | — | 3/3 no killing |
| CRM197 | 537.46 | — | 3/3 no killing |

(1)Amount of reconstituted toxin is calculated from 70% association of cDT-A to DT-B197, and 20% association of AE18 to DT-B197.
(2)One MLD is defined as 0.1 μg toxin/Kg in guinea pigs.
(3)Observations were made for two weeks after injection. In those animals that died, death occurred between 17 and 22 hr after injection. No killing is indicated for animals that were alive two weeks after injection.
*After the initial two-week observation period, one animal survived. To ascertain whether this was error, this animal, and a control animal, were injected at the same dosage (1.06 μg reconstituted toxin/Kg). Both animals died in 20 hr.

On Jan. 23, 1985, Applicants have deposited with the American Type Culture Collection, Rockville, Md., USA (ATCC) the plasmid pAE18, described hererin, ATCC accession no. 53008. The deposit was made from the Cetus Master Culture Collection and pAE18 was designated pPLOPAE18, CMCC No. 2215. This deposit was made under the provisions of the Budapest Treaty on the International Recognition of the Deposit of Microorganisms for the Purposes of Patent Procedure and the Regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

We claim:

1. A protein having immunological cross reactivity with diphtheria toxin, which comprises an enzymatically inactive diphtheria toxin A (DT-A) mutein, wherein the mutein is $Gly_{158}$DT-A.

2. The diphtheria toxin mutein of claim 1 in a mixture comprising a pharmaceutically acceptable carrier.

3. The diphtheria toxin mutein of claim 1 comprising DT-B covalently bound to said mutein.

* * * * *